United States Patent [19]
Clarke et al.

[11] 3,941,785
[45] Mar. 2, 1976

[54] IMIDAZO [5,1-F]-AS-TRIAZINES

[75] Inventors: Robert William Clarke; David Hartley; Alexander William Oxford, all of London, England

[73] Assignee: Allen & Hanburys Limited, London, England

[22] Filed: Dec. 26, 1973

[21] Appl. No.: 427,558

[30] Foreign Application Priority Data
Jan. 4, 1973 United Kingdom............... 553/73

[52] U.S. Cl............................. 260/249.5; 424/249
[51] Int. Cl.²......................................... C07D 253/08
[58] Field of Search.............................. 260/249.5

[56] References Cited
UNITED STATES PATENTS
3,840,537   10/1974   Garside et al................. 260/249.5

*Primary Examiner*—John M. Ford
*Attorney, Agent, or Firm*—Bacon & Thomas

[57] ABSTRACT
Compounds of the general formula:

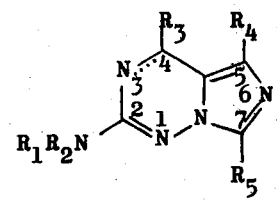

in which:
R₁ and R₂ which may be the same or different, represent a hydrogen atom or an alkyl group which may optionally be substituted by an aryl group, or represents an alkanoyl, aroyl or alkanesulphonyl group;

R₃ represents a hydrogen atom, or an alkyl group which may optionally be substituted by an aryl group, or represents an alkenyl, aryl or alkylthio group;

R₄ represents a hydrogen atom or an alkyl group; and

R₅ represents a hydrogen atom or an aryl or alkyl group, which alkyl group may optionally be substituted by a cycloalkyl group;

and physiologically acceptable salts and derivatives thereof and addition products formed by nucleophilic addition.

These compounds act as spasmolytics and phosphodiesterase inhibitors and have cardiotonic and diuretic properties. They are also of use in the treatment of skin disorders and gout.

64 Claims, No Drawings

IMIDAZO [5,1-F]-AS-TRIAZINES

RELATED APPLICATION

Application Ser. No. 300,749, filed 25th Oct. 1972, now U.S. Pat. No. 3,840,537 of Susan Constance Garside, David Hartley, Lawrence Henry Charles Lunts and Alexander William Oxford, entitled 'HETEROCYCLIC COMPOUNDS'

This invention relates to certain heterocyclic compounds having pharmacological activity and to processes for the preparation thereof as well as to pharmaceutical compositions containing them.

We have found that certain imidazo [5,1-f]- as-triazines and derivatives thereof act as spasmolytics and phosphodiasterase inhibitors and have cardiotonic and diuretic properties. They are therefore particularly useful as bronchodilators in the treatment diseases involving constriction of bronchial muscle, for example asthma and bronchitis and also for the treatment of pulmonary oedema and congestive heart failure. The compounds may also be useful for topical application in the treatment of skin disorders, for example psoriasis. A subsidiary utility possessed by certain of the compounds of the invention is in the treatment of gout since they are xanthene oxidase inhibitors.

The present invention therefore provides compounds of the general formula I:

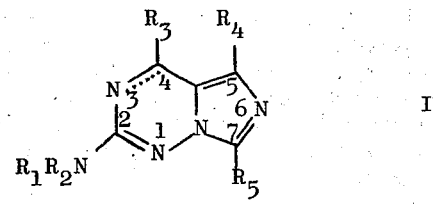

in which:

R$_1$ and R$_2$ which may be the same or different represent a hydrogen atom or an alkyl group which may optionally be substituted by an aryl group, or represents an alkanoyl, aroyl or alkanesulphonyl group.

R$_3$ represents a hydrogen atom, or an alkyl group which may optionally be substituted by an aryl group, or represents an alkenyl, aryl or alkylthio group.

R$_4$ represents a hydrogen atom or an alkyl group.

R$_5$ represents a hydrogen atom or an aryl or alkyl group which alkyl group may optionally be substituted by a cycloalkyl group containing 3 to 7 carbon atoms.

The above formula includes compounds in which there is a single bond in the 3,4-position or a double bond. It will be appreciated that when a single bond is present there is a hydrogen atom substituent on the nitrogen atom in the 3-position and the carbon atom in the 4-position.

The term alkyl when used above refers to a straight or branched alkyl group preferably containing 1 to 6 carbon atoms and the term alkenyl refers to straight or branched chain alkenyl groups containing 2 to 6 carbon atoms. The terms aryl and aroyl preferably refer to phenyl and benzoyl groups respectively and these groups may optionally be substituted by a halogen atom or one or more alkoxy groups.

The invention includes physiologically acceptable salts and derivatives thereof. Suitable salts include acid addition salts with inorganic or organic acids e.g. hydrochloride, sulphate, hydrogen sulphate methanesulphonate, hydrogen maleate, acetate.

Compounds of the general formula I may exist in several tautomeric forms and these are included within the scope of the invention.

The invention also includes addition products obtained by nucleophilic addition across the 3,4 double bond in compounds of the general formula I. Suitable compounds for addition include sodium bisulphite and compounds containing an active methylene group in particular 5,5-dimethylcyclohexane-1,3-dione, barbituric acid and p-methoxyacetophenone.

A preferred group of compounds according to the invention are those in which R$_1$ represents a hydrogen atom or alkyl (C$_{1-6}$) in particular methyl, ethyl, propyl, isobutyl 3-methyl butyl or aralkyl in particular benzyl, 3,4-dimethoxybenzyl, phenethyl or alkanoyl (C$_{1-6}$) in particular formyl, acetyl, butyryl, isovaleryl, or aroyl in particular benzoyl and 4-chlorobenzoyl or alkanesulphonyl, in particular methanesulphonyl.

R$_2$ represents a hydrogen atom or alkyl (C$_{1-4}$) in particular ethyl.

R$_3$ represents hydrogen or alkyl (C$_{1-4}$) in particular methyl, ethyl, or aralkyl in particular benzyl, phenethyl, or aryl in particular phenyl 4-methoxyphenyl, alkenyl in particular allyl, or alkylthio, in particular methylthio.

R$_4$ represents alkyl (C$_{1-4}$) in particular methyl.

R$_5$ represents alkyl (C$_3$-C$_6$) in particular propyl, isopropyl, isobutyl, sec-butyl, 2-methylbutyl, 3-methylbutyl or cyclopentylmethyl or cyclohexylmethyl, or aryl, in particular phenyl.

Particularly preferred compounds are those whose preparation is described in the examples.

The bronchodilating activity of these compounds is demonstrated by their action in the guinea pig in reducing bronchospasm induced by spasmogens such as histamine, 5-hydroxytryptamine and acetylcholine according to standard test procedures [Konsett, H & Rossler R. (1940). Versuchsanordung zu Untersuchungen an der Bronchial musculater. Arch. exp. Patho. Pharmakol., 195, 71–74]. For instance, 2-amino-5-methyl-7-propylimidazo[5,1-f]-as-triazine, hydrochloride is more active than standard non-adrenergic bronchodilators, such as choline theophyllinate. The compounds of the invention are inhibitors of the enzyme phosphodiesterase. For instance at a concentration of 5 × 10$^{-6}$ M, 2-amino-5-methyl-7-propylimidazo[5,1-f]-as-triazine, hydrochloride is about 8–10 times more potent than choline theophyllinate in inhibiting the degradative action of this enzyme on cyclic adenosine monophosphate, a humoral agent important in producing bronchodilation.

The compounds according to the invention may be formulated for use in human and veterinary medicine for therapeutic and prophylactic purposes. They may be used in the form of their physiologically acceptable salts if desired. Preferred salts include the hydrochloride, sulphate, maleate, tartrate, etc. Such compounds may be presented for use in the conventional manner with the aid of carriers or excipients and formulating agents as required, and with or without supplementary medicinal agents. The compositions may include solid and liquid preparations for oral use, suppositories or injections, or forms suitable for administration by inhalation. Oral administration is most convenient in the form of tablets. Injections may be formulated with the aid of physiologically acceptable carriers and agents as solutions, suspensions or as dry products for reconstitution before use. For administration by inhalation the compounds according to the invention are conveniently delivered in the form of an aerosol spray presentation from pressurised packs or a nebuliser. In the case of a pressurised aerosol the dosage unit may be determined by providing a valve to deliver a metered amount. A typical dose for treating asthma in humans is from 1–1200 mg. depending on the age, weight and condition of the patient and the route of administration.

The compounds according to the invention may be formulated in combination with compounds such as salbutamol and isoprenaline that have stimulant activity at β-adrenoreceptors. The provision of therapeutic compositions comprising as active ingredients, a compound according to the invention and a β-adrenoreceptor stimulant, in particular salbutamol, represents an important aspect of the invention. In some such mixtures a degree of synergism is seen between the active constituents.

As indicated above certain of the compounds show an action which may be advantageous in the treatment of gout. Particular compounds showing this activity are those of Examples 14a and 14b herein.

The compounds according to the invention may be prepared in principle by one main process.

In this process the compounds according to the invention in which there is a single bond in the 3,4 position are prepared from compounds of general formula II below such as by reduction. The compounds of formula II are described in copending application Ser. No. 300,749 filed Oct. 25, 1972 and now U.S. Pat. No. 3,840,537 or may be prepared in a manner similar to that described therein. The compounds according to the invention in which there is a double bond in the 3,4 position may be prepared by dehydrogenation of those compounds of the invention in which there is a single bond in that position. The compounds of formula II are represented below:

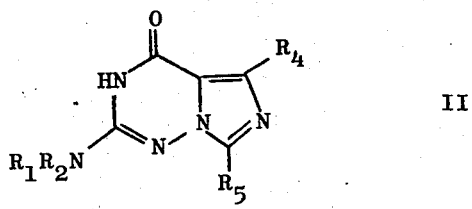

II

In these compounds the groups $R_1$, $R_2$, $R_4$ and $R_5$ have the meanings given above.

In addition $R_1$ and $R_2$ may represent groups which are converted on reduction to groups $R_1$ and $R_2$ within the meanings given and/or may represent groups which are convertible in a subsequent conversion to groups $R_1$ and $R_2$ within the meanings given. Another possibility consists in that the groups $R_1$ and $R_2$ may be converted from a group within the meaning given above in a subsequent conversion. Also in the reduction step the groups $R_1$ and $R_2$ within the above meaning may be formed in the reduction.

The conversion of the imidazotriazinone II into the compounds of the invention with a single bond in the 3,4 position may be carried out by reduction with a metal hydride such as lithium aluminium hydride, diborane or sodium dihydro-bis(2-methoxyethoxy) aluminate. The reaction may be carried out by heating in an aprotic solvent such as tetrahydrofuran, diglyme and diethyl digol. A suitable reaction temperature is from 80°–130°C preferably 100°–110°C. In an alternative conversion the imidazotriazinone II may be converted to a compound according to the invention in which there is a single bond in the 3,4 position via the alkylthio compound as described later.

The dehydrogenation of the compounds according to the invention in which there is a single bond in the 3,4 position may be carried out by heating with a noble metal catalyst, such as palladium oxide on charcoal, preferably in the presence of a high boiling solvent e.g., cymene or decalin.

Thus compounds according to the invention in which $R_1$ or $R_2$ represents an alkanoyl, aroyl or alkanesulphonyl group may be prepared from those compounds in which $R_1$ represents hydrogen and $R_2$ represents hydrogen or alkyl or aralkyl group by conventional acylation procedures. Preferred methods include the reaction with an alkanoyl halide e.g. acetyl or butyryl chloride in the corresponding alkanoic acid, or the reaction with an alkanoic or aromatic acid e.g. isovaleric or benzoic acid in methanesulphonyl chloride. The alkanesulphonyl derivative e.g. methanesulphonyl is most conveniently prepared from the reaction with the corresponding alkanesulphonic anhydride. These acylation reactions may be carried out with heating if desired. Those compounds of general formula I in which $R_1$ and/or $R_2$ are alkyl or aralkyl may be conveniently prepared from the corresponding compound in which $R_1$ or $R_2$ is alkanoyl or aroyl by reduction with a complex metal hydride e.g. lithium aluminium hydride. Alternatively these compounds may be prepared by the direct reduction of the imidazotriazinone II, in which $R_1$ or $R_2$ is an alkanoyl, aralkanoyl or aroyl group with a complex metal hydride as described above.

The imidazotriazines I in which $R_1$ represents an alkyl, alkanoyl or aroyl group and $R_2$ represents a hydrogen atom or an alkyl or aralkyl group may advantageously be prepared by dehydrogenation of the corresponding dihydroimidazotriazine I using the reaction conditions previously described.

Compounds according to the invention wherein $R_3$ is other than hydrogen may be conveniently compounds of the invention where $R_3$ is hydrogen and there is a double bond in the 3,4 position. Thus reaction with organometallic derivatives, e.g. $R_3$ MgHal or $R_3$Li in which $R_3$ is other than hydrogen, in an aprotic solvent such as diethyl ether or tetrahydrofuran gives the compounds of the invention in which there is a single bond in the 3,4 position. This reaction is particularly advantageous for preparing compounds in which $R_3$ is an alkyl, aralkyl, aryl or alkenyl group. The compounds in which there is a double bond in the 3,4 position may be obtained by dehydrogenation of the dihydro derivative as described above.

Addition products of compounds of the invention in which there is a double bond in the 3,4 position may be obtained by reaction with compounds containing an activated methylene group e.g. with barbituric acid or dimedone in water or aqueous alcohol. In the presence of a strong mineral acid such as hydrochloric acid, acetophenones also add across the 3,4 double bond to give corresponding dihydroimidazotriazine in which $R_3$ represents a phenacyl group.

Other classes of compounds also add across the 3,4 double bond, for example the addition of sodium metabisulphite gives an additional product in which there is a sulphonic acid group in the $R_3$ position.

Compounds of the general formula I in which $R_3$ is alkylthio group may be made by treating the corresponding imidazotriazinone II with phosphorus pentasulphide, followed by alkylation of the thione thus formed. The resulting alkylthio imidazotriazine I may be reduced to the corresponding dihydroimidazotriazine I $R_3 = H$. For example by reaction with sodium borohydride in a dipolar aprotic solvent such as N-methylpyrrolidone preferably with heating.

The procedure thus provides as indicated earlier an alternative method for the preparation of dihydroimidazotriazines I; $R_3 = H$ from the imidazotriazinone II.

The following examples illustrate the invention. Examples 1 to 23 describe the production of compounds of the invention. Example 24 describes the production of starting materials for Example 12. Example 25 describes the production of starting materials for Example 1.

EXAMPLE 1 a. 2-Amino-3,4-dihydro-5-methyl-7-propylimidazo[5,1-f]-as-triazine

2-Amino-5-methyl-7-propylimidazo[5,1-f]-as-triazin-4(3H)-one, hydrochloride (5 g.) (prepared according to Example 8 of application Ser. No. 300,749 and lithium aluminium hydride (2.9 g.) in tetrahydrofuran were heated under reflux for 78 hours, and cooled. Water (11.6 ml.) was added cautiously followed by aqueous sodium hydroxide (2.9 ml., 15%). The solid was filtered off, the filtrate was evaporated and the residue was triturated with ethyl acetate. The product was crystallised from ethyl acetate and had m.p. 242°–246°.

b. 2-Amino-3,4-dihydro-5-methyl-7-propylimidazo[5,1-f]-as-triazine, hydrochloride 2-Amino-3,4-dihydro-5-methyl-7-propylimidazo [5,1-f]-as-triazine (2 g.) in ethanol was treated with a solution of hydrogen chloride in ether. The solid was collected and crystallised from a mixture of ethanol and ether to give a white solid m.p. 263° (decomp.).

The following compounds were prepared by a similar procedure:

c. 2-Amino-3,4-dihydro-7-isopropyl-5-methylimidazo [5,1-f]-as-triazine, m.p. 284°–286° (recrystallised from a mixture of ethanol and ethyl acetate) and its hydrochloride m.p. 210°–12° were obtained from 2-amino-7-isopropyl-5-methylimidazo[5,1-f]-as-triazin-4(3H)-one (Example 25).

d. 2-Amino-3,4-dihydro-7-isobutyl-5-methylimidazo [5,1-f]-as-triazine, m.p. 258°–263° (crystallised from aqueous methanol) and its hydrochloride m.p. 225°–228° were obtained from 2-amino-7-isobutyl-5-methylimidazo[5,1-f]-as-triazin-4(3H)-one (Example 25).

e. 2-Amino-3,4-dihydro-5-methyl-7-phenylimidazo[5,1-f]-as-triazine, m.p. 262°–264° (recrystallised from a mixture of methanol and ethyl acetate) and its hydrochloride m.p. 328°–331° were obtained from 2-amino5-methyl-7-phenylimidazo[5,1-f]-as-triazin-4(3H)-one.

f. 2-Amino-7-cyclohexylmethyl-3,4-dihydro-5-methylimidazo[5,1-f]-as-triazine, m.p. 228°–230° (crystallised from a mixture of ethyl acetate and ether) was obtained from 2-amino-7-cyclohexylmethyl-5-methylimidazo[5,1-f]-as-triazin-4(3H)-one (Example 25).

g. 2-Amino-7-cyclohexylmethyl-3,4-dihydro-5-methylimidazo[5,1-f]-as-triazine, hydrogen maleate 2-Amino-7-cyclohexylmethyl-3,4-dihydro-5-methylimidazo[5,1-f]-as-triazine, (0.7 g.) in ethanol (50 ml.) was treated with maleic acid (0.4 g.) in ether (50 ml.) and the solid was collected and crystallised from a mixture of methanol and ethyl acetate to give a white solid, m.p. 130°–133°.

EXAMPLE 2 a. 2-Amino-3,4-dihydro-5-methyl-7(2-methylbutyl)imidazo[5,1-f]-as-triazine

2-Amino-5-methyl-7(2-methylbutyl)imidazo[5,1-f]-as-triazin-4(3H)-one (1.7 g.) and lithium aluminium hydride (0.9 g.) in diglyme (50 ml., freshly redistilled) were stirred and heated to 100° for 4.5 hours and cooled. Water (1 ml.) was added dropwise, followed by 2N sodium hydroxide (2 ml.) and water (1 ml.). The solid was filtered off, the filtrate was evaporated and the residue was crystallised from isopropanol. The product had m.p. 207°–213° (63%). It was converted to its hydrochloride, m.p. 203°–205.5° by treating a solution in ethanol with hydrogen chloride in ether.

In a similar way:

b. 2-Amino-7-cyclopentylmethyl-3,4-dihydro-5-methylimidazo[5,1-f]-as-triazine, m.p. 194°–198° (49%) was obtained from 2-amino-7-cyclopentylmethyl-5-methylimidazo[5,1-f]-as-triazin-4(3H)-one (AH 12963). It was converted to its hydrochloride, m.p. 255°–257°.

c. 2-Amino-3,4-dihydro-7-(3-methylbutyl)imidazo[5,1-f]-as-triazine, hydrochloride, m.p. 167°–172° (crystallised from a mixture of ethanol and ethyl acetate) was obtained from 2-amino-5-methyl-7(3-methylbutyl)-imidazo[5,1-f]-as-triazine-4(3H)-one (Example 25).

d. 2-Amino-3,4-dihydro-5-methyl-7(1-methylpropyl)imidazo[5,1-f]-as-triazine, m.p. 275°–290° and its dihydrochloride m.p. 270°–187° were prepared from 2-amino-5-methyl-7(1-methylpropyl)-imidazo[5,1-f]-as-triazine-4(3H)-one (AH 13014A)

EXAMPLE 3 a. 5-Methyl-7-propyl-2-propylaminoimidazo[5,1-f]-as-triazine, hydrochloride 3,4-Dihydro-5-methyl-7-propyl-2-propylaminoimidazo[5,1-f]-as-triazine (Example 12a) (1.44 g.) and palladium on charcoal catalyst (2.8 g., 10%) in p-cymene (100 ml.) were heated under reflux in p-cymene for 3 hours. The catalyst was filtered off and the filtrate was extracted with 2N hydrochloric acid (3 × 100 ml.). The extracts were neutralised with potassium carbonate and the mixture was extracted with ethyl acetate. The ethyl acetate solution was dried over magnesium sulphate, filtered and evaporated. The oil in ethyl acetate was treated with a solution of hydrogen chloride in ether. The solid was collected and had m.p. 201°–206°.

In a similar way, the following compounds were prepared:

b. 2-Benzylamino-5-methyl-7-propylimidazo[5,1-f]-as-triazine was prepared from 2-benzylamino-3,4-dihydro-5-methyl-7-propylimidazo[5,1-f]-as-triazine (Example 12b). It was converted into its hydrogen maleate which had m.p. 141°–142°.

c. 5-Methyl-2(2-phenethylamino)-7-propylimidazo[5,1-f]-as-triazine m.p. 124°–128° was prepared from 3,4-dihydro-5-methyl-2(2-phenethylamino)-7-propylimidazo[5,1-f]-as-triazine (Example 12c). It was converted to its hydrochloride m.p. 205°–206°.

d. 2-Isobutylamino-5-methyl-7-propylimidazo[5,1-f]-as-triazine, m.p. 87°–88°, was prepared from 2-isobutylamino-3,4-dihydro-5-methyl-7-propylimidazo[5,1-f]-as-triazine (Example 12f). It was converted to its hydrochloride, m.p. 201°–213°.

e. 2-(3,4-Dimethoxybenzylamino)5-methyl-7-propylimidazo[5,1-f]-as-triazine, m.p. 158°–160° was prepared from 2-(3,4-dimethoxybenzylamino)3,4-dihydro-5-methyl-7-propylimidazo[5,1-f]-as-triazine (Example 12d). It was converted to its hydrogen maleate, m.p. 118°–121°.

f. 2-Amino-7-isobutyl-5-methylimidazo[5,1-f]-as-triazine, m.p. 84°–86°, was prepared (72%) from 2-amino-3,4-dihydro-7-isobutyl-5-methylimidazo[5,1-f]-as-triazine (Example 1d). It was converted to its hydrogen maleate which was crystallised from a mixture of methanol and ether and had m.p. 178°–180°.

g. 2-Amino-4(p-methoxyphenyl)-5-methyl-7-propylimidazo[5,1-f]-as-triazine was prepared from 2-amino-3,4-dihydro-4(p-methoxyphenyl)-5-methyl-7-propylimidazo[5,1-f]-as-triazine (Example 14b). It was converted to its hydrochloride, which was crystallised from a mixture of ethanol and ether and had m.p. 224°–226° (21%).

h. 2-Amino-4,5-dimethyl-7-propylimidazo[5,1-f]-as-triazine, was prepared from 2-amino-3,4-dihydro-4,5-dimethyl-7-propylimidazo[5,1-f]-as-triazine (Example 16c). It was converted into its hydrogen maleate which had m.p. 155°–156°.

EXAMPLE 4

2-Amino-5-methyl-7-propylimidazo[5,1-f]-as-triazine, hydrochloride

2-Amino-3,4-dihydro-5-methyl-7-propylimidazo[5,1-f]-as-triazine (Example 1a) (2 g.) and palladium on charcoal catalyst (3 g.) in decalin (100 ml.) were heated under reflux for 6 hours. The mixture was filtered and cooled and extracted with 2N hydrochloric acid (2 × 100 ml.). The extracts were made alkaline with 2N sodium hydroxide and extracted with ethyl acetate. The ethyl acetate solution was dried over magnesium sulphate, filtered and evaporated and the residue was chromatographed on silica (50 ml.) to give a yellow solid (0.32g.), 5N sodium hydroxide (2.5 ml) and water (7.5 ml.). The solid was filtered off and extracted with ethyl acetate (3 × 100 ml.). The extracts were dried and evaporated and the solid was crystallized from ethyl acetate and had m.p. 157°–167°, 1.74 g. (The hydrochloride had m.p. 271°–276°, and was prepared in ethyl acetate by addition HCl/Et$_2$O).

EXAMPLE 5

N-(5-Methyl-7-propylimidazo[5,1-f]-as-triazin-2-yl)-methane-sulphonamide

N-(3,4-Dihydro-5-methyl-7-propylimidazo[5,1-f]-as-triazin-2-yl)-methane sulphonamide, methanesulphonate (Example 8) in water was treated with sodium bicarbonate. The solution was evaporated and the residue was extracted with hot isopropanol. The extract was evaporated to give N-(3,4-dihydro-5-methyl-7-propylimidazo[5,1-f]-as-triazin-2-yl)-methane sulphonamide. This sulphonamide (1.5 g.) and 10% palladium on charcoal catalyst (3g, 10%) in p-cymene (100 ml) were heated under reflux for 2.5 hours and cooled. The catalyst was filtered off and the filtrate was evaporated. The residue was triturated with ethyl acetate to give a yellow solid, m.p. 191°–195°. It was converted into its hydrogen maleate salt m.p. 165°–168°.

EXAMPLE 6 a. N-(3,4-Dihydro-5-methyl-7-propylimidazo[5,1-f]-as-triazin-2-yl)benzamide, hydrogen maleate 2-Amino-3,4-dihydro-5-methyl-7-propylimidazo[5,1-f]-as-triazine (Example 1a) (1.5 g.) and benzoic acid (2.46 g.) in methanesulphonyl chloride (10 ml.) were heated to 140° to 4 hours and cooled. The mixture was shaken several times with ether and poured into aqueous sodium carbonate. The mixture was extracted with ethyl acetate, the extracts were dried over anhydrous magnesium sulphate, filtered and evaporated. The residual solution was dissolved in ethyl acetate and maleic acid (1 g.) in ethyl acetate (40 ml.) was added followed by ether (50 ml.). The solid was collected and crystallized from a mixture of isopropanol and ether and had m.p. 183°–185°.

In a similar way:

b. N-(3,4-Dihydro-5-methyl-7-isobutylimidazo[5,1-f]-as-triazin-2-yl)-p-chlorobenzamide, m.p. 236°–239° was prepared from 2-amino-3,4-dihydro-5-methyl-7-isobutylimidazo[5,1-f]-as-triazine (Example 1d) and P-chlorobenzoic acid. It was converted into its hydrochloride salt m.p. 240°–247°.

c. N-(3,4-Dihydro-5-methyl-7-propylimidazo[5,1-f]-as-triazin-2-yl) isovaleramide hydrochloride m.p. 233°–235° (crystallised from a mixture of isopropanol and ether) was prepared using isovaleric acid in place of benzoic acid.

EXAMPLE 7

N-Ethyl-N-(3,4-Dihydro-5-methyl-7-propylimidazo[5,1-f]-as-triazin-2-yl)acetamide, hydrochloride 2-Ethylamino-3,4-dihydro-5-methyl-7-propylimidazo[5,1-f]-as-triazine (Example 12e) (1.1 g.) and acetyl chloride (1.65 ml.) in glacial acetic acid (10 ml.) were heated on a steam bath for 16 hours. The acetic acid was distilled off and the residue was crystallised from a mixture of isopropanol and ether to give a solid, m.p. 190°–192° (73%).

EXAMPLE 8

N-(3,4-Dihydro-5-methyl-7-propylimidazo[5,1-f]-as-triazin-2-yl)-methanesulphonamide, methanesulphonate 2-Amino-3,4-dihydro-5-methyl-7-propylimidazo[5,1-f]-as-triazine, hydrochloride (Example 1b) (2.5 g.) in methanesulphonic anhydride (12 g.) was heated at 140° for 2 hours and cooled. The mixture was triturated several times with ether and the solid was crystallised from ethanol to give the product, m.p. 209°–222° (68%).

EXAMPLE 9 a. N-(3,4-Dihydro-5-methyl-7-propylimidazo[5,1-f]-as-triazin-2-yl)acetamide, hydrochloride 2-Amino-3,4-dihydro-5-methyl-7-propylimidazo[5,1-f]-as-triazine (Example 1a) (1.9 g.) and acetyl chloride (1.8 g.) in acetic acid (20 ml., glacial) were heated at 100° for 3 hours. The solution was evaporated under reduced pressure and the residue was crystallised from a mixture of ethanol and ethyl acetate to give a white solid m.p. 302°.

The followig compounds were prepared in a similar way:

b. N-(3,4-Dihydro-7-isobutyl-5-methylimidazo[5,1-f]-as-triazin-2-yl)acetamide, m.p. 269°–271° (crystallised from a mixture of ethanol and ether) (Starting material Example 1d).

c. N-(3,4-Dihydro-7-isopropyl-5-methylimidazo[5,1-f]-as-triazin-2-yl)acetamide, m.p. 319°–321° (crystallised from a mixture of ethanol and ethyl acetate) (Starting material Example 1e).

d. N-(3,4-Dihydro-4,5-dimethyl-7-propylimidazo[5,1-f]-as-triazin-2-yl)acetamide hydrochloride m.p. 272°–274° (crystallised from a mixture of ethanol and ethyl acetate) (Starting material Example 16c).

EXAMPLE 10 a. N-(3,4-Dihydro-5-methyl-7-propylimidazo[5,1-f]-as-triazin-2-yl)formamide

2-Amino-3,4-dihydro-5-methyl-7-propylimidazo[5,1-f]-as-triazine (Example 1a) (2.2 g.) in formic acid (50 ml., 99°) was heated under reflux for 24 hours and evaporated under reduced pressure. The residue was stirred with 2N sodium carbonate and the solid was collected and dried and had m.p. 188.5°–190.5°. Its hydrogen maleate salt had m.p. 159°–161° (crystallised from a mixture of methanol and ether).

b. In a similar manner N-(3,4-dihydro-5-methyl-7-isobutylimidazo[5,1-f]-as-triazin-2-yl)formamide m.p. 209°–211° (crystallised from ethyl acetate) and its hydrochloride m.p. 257°–258° (crystallised from a mixture of ethanol and ethyl acetate).

EXAMPLE 11

N-(3,4-Dihydro-5-methyl-7-propylimidazo[5,1-f]-as-triazin-2-yl)butyramide, hydrochloride 2-Amino-3,4-dihydro-5-methyl-7-propylimidazo[5,1-f]-as-triazine (Example 1a) (2 g.) and butyryl chloride (11 ml.) in butyric acid (50 ml.) were heated under reflux for 5.5 hours and cooled with ice. 5N sodium hydroxide was added slowly and until the mixture was alkaline and the solid was filtered off. The filtrate was evaporated under reduced pressure and the residue was stirred with aqueous sodium bicarbonate. The mixture was extracted with ethyl acetate and the extract was dried over magnesium sulphate, filtered and evaporated. The residue was crystallised from methanol to give a white solid, m.p. 161°–162°.

EXAMPLE 12 a. 3,4-Dihydro-5-methyl-7-propyl-2-propylaminoimidazo[5,1f]-as-triazine, hydrochloride N-(3,4-Dihydro-4-oxo-5-methyl-7-propylimidazo[5,1-f]-as-triazin-2-yl) propionamide, hydrochloride (5.08g.) and lithium aluminium hydride (5 g.) in dry tetrahydrofuran (300 ml.) were stirred and heated under reflux for 60 hours and cooled. Water (5 ml.) was added dropwise followed by 5N sodium hydroxide (5 ml.) and water (15 ml.). The solid was filtered off and the filtrate was evaporated. The residue was dissolved in ethanol and hydrogen chloride in ether was added to give a solid that was crystallised from a mixture of ethanol and ethyl acetate and had m.p. 264°–272°.

In a similar manner:

b. 2-Benzylamino-3,4-dihydro-5-methyl-7-propylimidazo[5,1-f]-as-triazine, hydrochloride was prepared from N-(3,4-Dihydro-4-oxo-5-methyl-7-propylimidazo[5,1-f]-as-triazin-2-yl)benzamide and had m.p. 235°–240°.

c. 3,4-Dihydro-5-methyl-2(2-phenylethylamino)-7-propylimidazo[5,1-f]-as-triazine, hydrochloride, m.p. 195°–200°, was obtained from N-(3,4-dihydro-4-oxo-5-methyl-7-propylimidazo[5,1-f]-as-triazin-2-yl)phenylacetamide, methanesulphonate.

d. 3,4-Dihydro-2-(3,4-dimethoxybenzylamino)-5-methyl-7-propylimidazo[5,1f]-as-triazine m.p. 120°–123° (66%) was prepared from N-(3,4-dihydro-4-oxo-5-methyl-7-propylimidazo[5,1-f]-as-triazin-2-yl)-3,4-dimethoxybenzamide, methanesulphonate.

e. 2-Ethylamino-3,4-dihydro-5-methyl-7-propylimidazo[5,1-f]-as-triazine, hydrogen maleate m.p. 129°–130.5° was obtained from N-(3,4-Dihydro-5-methyl-4-oxo-7-propylimidazo[5,1-f]-as-triazin-2-yl)acetamide hydrochloride.

f. 3,4-Dihydro-2-iso-amylamino-5-methyl-7-propylimidazo[5,1-f]-as-triazine m.p. 157°–167° and its hydrochloride m.p. 271°–276° are prepared from N-(3,4-Dihydro-4-oxo-5-methyl-7-propylimidazo[5,1-f]-as-triazin-2-yl)isobutyramide hydrochloride.

EXAMPLE 13

2-Methylamino-3,4-dihydro-5-methyl-7-isobutylimidazo [5,1f]-as-triazine, hydrochloride N-(3,4-Dihydro-5-methyl-7-isobutylimidazo[5,1-f]-as-triazin-2-yl)formamide (Example 10b) (1 g.) and lithium aluminium hydride (0.9 g.) in dry tetrahydrofuran (60 ml.) were heated under reflux for 4.5 hours, and cooled. Water (1 ml.) was added dropwise followed by 5N sodium hydroxide (1 ml.) and water (3 ml.). The mixture was filtered and the filtrate was evaporated. The residue in ethanol was treated wiith hydrogen chloride in ether and the solid was crystallised from a mixture of ethanol and ethyl acetate and had m.p. 290°–293°(d).

EXAMPLE 14

2-Amino-3,4-dihydro-5-methyl-4-phenyl-7-propylimidazo[5,1f]-as-triazine, hydrochloride 2-Amino-5-methyl-7-propylimidazo[5,1-f]-as-triazine (Example 4) (1.9 g.) in dry tetrahydrofuran (75 ml) was added to phenyl magnesium bromide (from bromobenzene (7.85 g.) and magnesium (1.2 g.) in ether (60 ml.) and the mixture stirred for 5 hours. Saturated aqueous ammonium sulphate (50 ml.) was added and the organic layer was separated, dried over magnesium sulphate and filtered and concentrated. The solid was crystallised from aqueous ethanol and dried and had m.p. 278°–279°. The solid in ethanol was treated with hydrogen chloride in ether and the solid was collected and crystallised from a mixture of ethanol and ether and had m.p. 179°–181°.

b. In a similar way, 2-amino-3,4-dihydro-4(p-methoxyphenyl)-5-methyl-7-propylimidazo[5,1f]-as-triazine, hydrochloride was prepared from p-methoxyphenyl magnesium bromide and 2-amino-5-methyl-7-propylimidazo[5,1-f]-as-triazine (Example 4) and had m.p. 178°–181°.

EXAMPLE 15

4-Allyl-2-amino-3,4-dihydro-5-methyl-7-propylimidazo[5,1f]-as-triazine, hydrogen maleate Allyl chloride (9.9 ml) in anhydrous tetrahydrofuran (75 ml) was added to magnesium turnings (2.9 g.) in anhydrous tetrahydrofuran (30 ml.). When the reaction was complete, 2-amino-5-methyl-7-propylimidazo[5,1-f]-as-triazine (Example 4) (1.93 g.) in anhydrous tetrahydrofuran (20 ml.) was added and the mixture was stirred for 30 minutes. Ammonium chloride (6.5 g.) in water (25 ml.) was added and the organic layer was separated, dried over magnesium sulphate, filtered and evaporated. The solid in ethyl acetate (100 ml.) was treated with maleic acid (1.7 g) in ethyl acetate (100 ml.) and the solid was collected and crystallised from a mixture of isopropanol and ether and had m.p. 229°–231°.

EXAMPLE 16 a. 2-Amino-3,4-dihydro-4,5-dimethyl-7-isobutylimidazo-[5,1-f]-as-triazine, hydrochloride 2-Amino-3,4-dihydro-7-isobutyl-5-methylimidazo [5,1-f]-as-triazine (Example 3f) (2 g.) in dry ether (50 ml) was added to methyl magnesium iodide (prepared from magnesium (1.17 g.) and methyl iodide (2.56 ml.)) in ether (50 ml.). The mixture was heated under reflux for 2 hours and kept overnight. Aqueous ammonium chloride (100 ml., 1%) was added and the ether layer was separated. The aqueous layer was kept for 4 days and the solid that crystallised was collected and crystallised from a mixture of ethanol and ethyl acetate and had m.p. 265°–267°. (The hydrochloride had m.p. 142°–143°).

b. In a similar manner, 2-amino-3,4-dihydro-4-ethyl-5-methyl-7-propylimidazo[5,1-f]-as-triazine was prepared from 2-amino-5-methyl-7-propylimidazo[5,1-f]-as-triazine (Example 4) and ethylmagnesium bromide. It was isolated as its hydrochloride salt which was crystallised from a mixture of isopropanol and ether and had m.p. 170°–172°.

c. 2-Amino-3,4-dihydro-4,5-dimethyl-7-propylimidazo[5,1-f]-as-triazine m.p. 268°–271° (crystallised from ethyl acetate) and its hydrochloride m.p. 252°–254° (crystallised from a mixture of ethanol and ether) were prepared from 2-amino-5-methyl-7-propylimidazo[5,1-f]-as-triazine (Example 4) and methyl magnesium iodide.

EXAMPLE 17

N-(4-Benzyl-3,4-dihydro-5-methyl-7-propylimidazo[5,1-f]-as-triazin-2-yl)acetamide, hydrochloride 2-Amino-5-methyl-7-propylimidazo[5,1-f]-as-triazine (Example 4) (1.9 g.) was added to benzyl magnesium chloride (prepared from benzyl chloride (6.3 g.) and magnesium (1.2 g.)) in ether (400 ml.), and the mixture was stirred for 4 hours at room temperature. Aqueous ammonium chloride (50 ml., 20%) was added and the aqueous layer was separated and extracted with ethyl acetate. The extracts were dried over magnesium sulphate, filtered and evaporated and the residue was chromatographed on silica gel (100 g.). Fractions eluted with ethyl acetate were discarded. The fractions eluted with a mixture of ethyl acetate and methanol (4:1) were evaporated to give 2-amino-4-benzyl-3,4-dihydro-5-methyl-7-propylimidazo [5,1-f]-as-triazine as a gum (0.83 g.). This gum (0.7 g.) and acetyl chloride (0.3 ml.) in glacial acetic acid (10 ml.) were heated at 100° for 2.5 hours. Acetic acid was distilled off and the residue was crystallised from a mixture of ethanol and ethyl acetate to give a white solid, m.p. 240°–241°.

EXAMPLE 18 a. 5-(2-Amino-3,4-dihydro-5-methyl-7-propylimidazo[5,1-f]-as-triazin-4-yl)-barbituric acid Barbituric acid (1.36 g.) and 2-amino-5-methyl-7-propylimidazo[5,1-f]-as-triazine (Example 4) (2 g.) in water (60 ml.) were stirred for 1.75 hours. The solid was collected and crystallised from water to give a solid m.p. 256°–258°.

b. 5-(2-Amino-3,4-dihydro-5-methyl-7-propylimidazo[5,1-f]-as-triazin-4-yl)barbituric acid, hydrochloride 5(2-Amino-3,4-dihydro-5-methyl-7-propylimidazo [5,1-f]-as-triazin-4-yl)barbituric acid (0.5 g.) in ethanol (10 ml.) was treated with a solution of hydrogen chloride in ether. The solid was collected and crystallised from a mixture of methanol and ether and had m.p. 200°–205°.

EXAMPLE 19

2-Amino-3,4-dihydro-4(4,4-dimethyl-2,6-dioxocyclohexyl)-5-methyl-7-propylimidazo[5,1-f]-as-triazine 2-Amino-5-methyl-7-propylimidazo[5,1-f]-as-triazine (Example 4) (1 g.) in aqueous ethanol (20 ml., 1:1) and 5,5-dimethylcyclohexane-1,3-dione (1 g.) in aqueous ethanol (20 ml., 1:1) were mixed. The solid was collected and dried and had m.p. 243°.

EXAMPLE 20

2-Amino-3,4-dihydro-4(p-methoxyphenacyl)-5-methyl-7-propylimidazo[5,1-f]-as-triazine, hydrochloride 2-Amino-5-methyl-7-propylimidazo[5,1-f]-as-triazine (Example 4) (1.9 g.), p-methoxyacetophenone (1.65 g.) and concentrated hydrochloric acid (2 ml.) in ethanol (50 ml.) were heated under reflux for 1.5 hours. The solvent was distilled off and the residue was treated with 2N sodium carbonate. The mixture was extracted with ethyl acetate and the extract was dried over magnesium sulphate, filtered and evaporated. The residue was crystallised from a mixture of ethyl acetate and light petroleum and had m.p. 193°–195°. The solid in ethanol (20 ml.) was treated with hydrogen chloride in ether. The mixture was further diluted with ether and the solid that crystallised from a mixture of isopropanol and ether and had m.p. 122°.

EXAMPLE 21

2-Amino-3,4-dihydro-5-methyl-7-propylimidazo[5,1-f]-as-triazine-4-sulphonic acid Sodium metabisulphite (1.5 g.) in water (45 ml.) was added to 2-amino-5-methyl-7-propylimidazo[5,1-f]-as-triazine (Example 4) (1.9 g.) in ethanol (20 ml.). The solid was collected and dried and had m.p. 232°–234°.

EXAMPLE 22

2-Diethylamino-5-methyl-7-propylimidazo[5,1-f]-as-triazine, hydrochloride

N-Ethyl-N-(3,4-dihydro-5-methyl-7-propylimidazo [5,1-f]-as-triazin-2-yl)acetamide, hydrochloride (Example 7) (4.1 g.) and lithium aluminium hydride (3.3 g.) in a mixture of dimethyl digol (130 ml.) and diethyl digol (150 ml.) were heated under reflux for 24 hours and cooled. Water (3.37 ml.) was added followed by aqueous sodium hydroxide (3.3 ml.) and water (9.8 ml.). The solid was filtered off and the filtrate was evaporated. The residue was chromatographed on active alumina (300 g.) using ethyl acetate as eluent. The first 400 ml. of eluate was discarded and a fraction (900 ml.) then collected was evaporated to give an oil. This oil (1.1 g.) and palladium on charcoal catalyst (1 g., 10%) in p-cymene (60 ml.) were heated under reflux for 30 minutes, cooled and filtered. The filtrate was shaken with 2N hydrochloric acid (3 × 25 ml.) and the aqueous acid solution was separated and neutralised by addition of potassium carbonate. The mixture was extracted with ethyl acetate and the extracts were dried over magnesium sulphate, filtered and evaporated. The residue in ether was treated with a solution of hydrogen chloride in anhydrous ether. The solid crystallised from a mixture of ethyl acetate and ether to give the product, m.p. 83°–84°.

EXAMPLE 23

2-Amino-5-methyl-4-methylthio-7-propylimidazo[5,1-f]-as-triazine, hydrochloride a. 2-amino-5-methyl-7-propylimidazo[5,1-f]-as-triazine-4(3H)-thione, hydrochloride.

2-amino-5-methyl-7-propylimidazo[5,1-f]-as-triazin-4(3H)-one hydrochloride (10 g.) and phosphorus pentasulphide (14 g.) in pyridine (150 ml.) were heated under reflux for 18 hours. The pyridine was distilled off and the residue was dissolved in 2N sodium hydroxide. Glacial acetic acid was added and the solid was collected and dissolved in ethanol. A solution of hydrogen chloride in ether was added and the solid was collected and crystallised from a mixture of ethanol and ether. It had m.p. 290°–292°.

b. 2-amino-5-methyl-4-methylthio-7-propylimidazo[5,1-f]-as-triazine 2-amino-5-methyl-7-propylimidazo[5,1-f]-as-triazine-4(3H)-thione, hydrochloride (0.65 g.) in a slight excess of 2N sodium hydroxide was treated with iodomethane (0.4 g.) and the mixture was stirred 2 hours at room temperature. The solid was collected and crystallised from aqueous ethanol and had m.p. 139°–140°. Its hydrochloride melted at 207°–208°.

c. 2-amino-3,4-dihydro-5-methyl-7-propylimidazo[5,1-f]-as-triazine, hydrochloride.

2-amino-5-methyl-4-methylthio-7-propylimidazo[5,1-f]-as-triazine (1 g.) and sodium borohydride (0.5 g.) in N-methylpyrrolidone (25ml.) were heated on a steam bath for 7 hours. Water (150 ml.) was added and the mixture was extracted continuously with ethyl acetate for 3 hours. The extract was dried over magnesium sulphate, filtered and evaporated and the residue was purified by chromatography on silica gel using a mixture of ethyl acetate and ethanol as eluent. The eluate was evaporated and the residue in ethanol was treated with a solution of hydrogen chloride in ether. The solid was crystallised from a mixture of ethanol and ether and had m.p. 251°.

EXAMPLE 24

N-(3,4-Dihydro-5-methyl-4-oxo-7-propylimidazo[5,1-f]-as-triazin-2-yl)-2-phenylacetamide, methanesulphonate A mixture of 2-amino-5-methyl-7-propylimidazo[5,1-f]-as-triazin-4(3H)-one hydrochloride (3.0 g.), methanesulphonyl chloride (1.6 ml, 2.36 g.) and phenylacetic acid (15 g.) was stirred and heated at 140° for 3½ hours. The mixture was allowed to cool then diluted with ether (75 ml). An oil separated which changed to a buff solid. This was collected, washed with ether, and recrystallised from ethanol-ethyl acetate to give the methanesulphonate salt of the phenylacetamide as white needles, m.p. 214°–219°.

By a similar procedure was prepared:
N-(3,4-Dihydro-5-methyl-4-oxo-7-propylimidazo[5,1-f]-as-triazin-2-yl) propionamide, hydrochloride, m.p. 252°–257° (sinters at 248°) (from ethanol-ethyl acetate).
N-(3,4-Dihydro-4-oxo-5-methyl-7-propylimidazo[5,1-f]-as-triazin-2-yl) isobutyramide, hydrochloride, m.p. 248°–255° (from ethanol).
N-(3,4-Dihydro-4-oxo-5-methyl-7-propylimidazo[5,1-f]-as-triazin-2-yl) benzamide, methanesulphonate, m.p. 198°–200.5° (from ethyl acetate).
N-(3,4-Dihydro-4-oxo-5-methyl-7-propylimidazo[5,1-f]-as-triazin-2-yl)-3,4-dimethoxybenzamide, methanesulphonate, m.p. 211°–213.5° (from ethanol).

In these reactions toluene was used as a co-solvent.

EXAMPLE 25

2-Amino-7-isopropyl-5-methylimidazo[5,1-f]-as-triazin-4-one

N-[1-(3-Amino-2-benzyl-2,5-dihydro-5-oxo-as-triazin-6-yl) ethyl]isobutyramide

3-Amino-1-benzyl-6 (1-Aminoethyl) as-triazin-5-one (1 g.) and isobutyric anhydride (0.75 ml.) in 1,4-dioxan (20 ml.) were stirred for some hours at room temperature. Ether was added and the solid was collected and crystallised from ethyl acetate. It had m.p. 226°–228°.

In a similar way N-[1-(3-Amino-2-benzyl-2,5-dihydro-5-oxo-as-triazin-6-yl)ethyl]isovaleramide m.p. 149.5° was prepared from 3-amino-1-benzyl-6(1-aminoethyl)-as-triazin-5-one and isovaleric anhydride.

N-[1-(3-Amino-2-benzyl-2,5-dihydro-5-oxo-as-triazin-6-yl)ethyl]-cyclohexylacetamide, m.p. 200°–202° (recrystallised from methanol) was obtained from 3-amino-1-benzyl-6(1-aminoethyl)-as-triazin-5-one and cyclohexyl-acetic anhydride.

N-[1-(3-Amino-2-benzyl-2,5-dihydro-5-oxo-as-triazin-6-yl)-ethyl]-4 methyl valeramide 4-Methylvaleric acid (0.5 g.) and methylamine (0.44 g.) in dioxan (25 ml.) was treated with piraloyl chloride (0.5 g.) in dioxan (25 ml.) and the mixture was stirred 1 hour at room temperature. The solid was filtered off and 3-amino-1-benzyl-6(1-aminoethyl)-as-triazin-5-one (1 g.) was added. The mixture was stirred for 24 hours at room temperature and ether (300 ml.) was added. The solid was collected and crystallised from ethanol. The product had m.p. 188°–190°.

In a similar way the following compounds were prepared from 3-amino-1-benzyl-6(1-aminoethyl)-as-triazin-5-one and the appropriate acid.

N-[1-(3-Amino-2-benzyl-2,5-dihydro-5-oxo-as-triazin-6-yl)ethyl]-3-methyl valeramide, m.p. 212°–215° (from ethanol).

N-[1-(3-Amino-2-benzyl-2,5-dihydro-5-oxo-as-triazin-6-yl)ethyl]-2-methyl butyramide, m.p. 233°–235° (from ethanol).

N-[1-(3-Amino-2-benzyl-2,5-dihydro-5-oxo-as-triazin-6-yl)ethyl]-cyclopentylacetamide, m.p. 195°–196.5° (from a mixture of ethanol and ether).

N-[1-(3-Amino-4,5-dihydro-5-oxo-as-triazin-6-yl)ethyl]-isobutyramide, hydrochloride N-[1-(3-Amino-2-benzyl-2,5-dihydro-5-oxo-as-triazin-6-yl)ethyl]-isobutyramide (14.2 g.) 2N hydrochloric acid (50 ml.) and palladium oxide on charcoal catalyst (2 g.) and ethanol (250 ml.) was shaken with hydrogen at atmosphere pressure and room temperature. The catalyst was filtered off and the filtrate was evaporated to give the product, m.p. 310°–314°.

In a similar way the following compounds were prepared:

N-[1-(3-Amino-4,5-dihydro-5-oxo-as-triazin-6-yl)ethyl]isovaleramide, m.p. 281°.

N-[1-(3-Amino-4,5-dihydro-5-oxo-as-triazin-6-yl)ethyl]cyclohexylacetamide, m.p. 200°–202°.

N-[1-(3-Amino-4,5-dihydro-5-oxo-as-triazin-6-yl)ethyl] 4-methylveleramide, m.p. 280°–283°.

N-[1-(3-Amino-4,5-dihydro-5-oxo-as-triazin-6-yl)ethyl]-3-methylvaleramide, 298°–300°.

N-[1-(3-Amino-4,5-dihydro-5-oxo-as-triazin-6-yl)ethyl]-2-methylbutyramide, m.p. 268°–270°.

N-[1-(3-Amino-4,5-dihydro-5-oxo-as-triazin-6-yl)ethyl]cyclopentylacetamide, m.p. 313°–315°.

2-Amino-7-isopropyl-5-methylimidazo[5,1-f]-as-triazin-4(3H)-one

N-[1-(3-Amino-4,5-dihydro-5-oxo-as-triazin-6-yl)ethyl]isobutyramide (1 g.) in polyphosphoric acid (10 g.) was heated at 150° for 1 hour, cooled and poured onto ice. The solution was neutralised by the addition of sodium carbonate and extracted with ethyl acetate. The extract was dried over magnesium sulphate filtered and evaporated to give the product, m.p. 310°–314°.

In a similar way, the following compounds were prepared:

2-Amino-7-isobutyl-5-methylimidazo[5,1-f]-as-triazin-4(3H)-one, m.p. 251°.

2-Amino-7-cyclohexylmethyl-5-methylimidazo[5,1-f]-as-triazin-4(3H)-one m.p. 278°–283°.

2-Amino-5-methyl-7(3-methylbutyl)imidazo[5,1-f]-as-triazin-4(3H)-one m.p. 251°–255°.

2-Amino-5-7(2-methylbutyl)imidazo[5,1-f]-as-triazin-4(3H)-one m.p. 220°–232°.

2-Amino-5-methyl-7(1-methylbutyl)imidazo[5,1-f]-as-triazin-4(3H)-one, m.p. 262°–268°.

2-Amino-7-cyclopentylmethyl-5-methylimidazo[5,1-f]-as-triazin-4(3H)-one, m.p. 159°–160°.

EXAMPLE 26

This Example gives representative formulations containing as active ingredient 2-amino-3,4-dihydro-7-isobutyl-5-methylimidazo[5,1-f]-as-triazine referred in the Examples as AH 11554. This compound is used in the form of the hydrochloride which is referred to as AH 11554A.

Injection — containing 10 mg AH 11554 per ml

| Formula | per ml | |
|---|---|---|
| AH 11554 | 11.76 | mg (equivalent to 10 mg AH 11554 base) |
| Sodium chloride | 6.1 | mg |
| Water for Injections to | 1.0 | ml |

Method of manufacture

Dissolve the AH 11554 and the sodium chloride in 90% of the water for injections. When solution is complete make up to volume with further water for injections. Filter through a suitable clarifying filter.

The solution can then either be packed into 1 ml neutral glass snap-ring ampoules and sterilised by heating in an autoclave or by filtration or may be prepared aseptically.

Tablets

| Formula | mg/tablet | | mg/tablet | |
|---|---|---|---|---|
| AH 11554 | 29.4 | mg | 11.8 | mg |
| (equivalent to AH 11554 base) | 25 | mg | 10 | mg |
| Lactose B.P. | 146.6 | | 120.2 | |
| Maize starch B.P. | 20.0 | | 15.0 | |
| Maize starch as 5% paste | 2.0 | | 1.5 | |
| Magnesium stearate B.P. | 2.0 | | 1.5 | |
| Final Tablet Weight | 200 | | 150 | |

Method of Manufacture

Blend together the milled AH 11554 and Lactose. Prepare the requisite quantity of 5% Starch Paste and add to the mixed powder and mix until a uniform damp cohesive mass is formed. Granulate this mass by passing through a suitable mill or sieve to produce discrete granulates. Dry the granules in either a fluid bed drier or on trays in a hot air oven at a temperature of about 50°C. After drying pass the granules through a 30 mesh B.S. sieve to break up aggregates.

Mix together the dried granules, the Maize Starch and the Magnesium Stearate and compress on a suitable tablet press. The tablets containing 30 mg AH 11554 each weigh about 200 mg and are 8.0 mm in diameter, those containing 10 mg AH 11554 each weigh about 156 mg and are 7.0 mm in diameter.

Inhalation Aerosol

| Formulation | mg/metered dose | |
|---|---|---|
| 1. AH 11554 base (micronised) | 0.5 | |
| 2. Sorbiton trioleate | 0.5 | |
| 3. Trichlorofluoromethane B.P. | 23 | |
| 4. Dichlorodifluoromethane B.P. | 85 | mg |

Method of Manufacture

Disperse the micronised AH 11554 base in the trichlorofluoromethane with the Sorbitan trioleate. Fill the requisite volume of this dispersion into suitable aerosol cans and seal by means of a suitable metering valve. Pressurise the containers by injecting the dichlorofluoromethane through the valve.

In an alternative formula components 1, 3 and 4 are identical to 1, 3 and 4 identified above but 2 is replaced by Emulsifier YN 0.01 mg.

Topical Preparation

| Formula | % w/v |
|---|---|
| AH 11554 base | 1.0 |
| Cetomacrogol cream B.P.C. to | 100.0 |

Method of Manufacture

Prepare the cetomacrogol cream as directed in the B.P.C. 1968. Disperse the finely divided AH 11554 in a proportion of the cream and carefully incorporate this concentrated mixture into the remainder of the cream base. Subdivide into suitable lacquered aluminium tubes.

In an alternative formulation salbutamol sulphate is used as additional active ingredient in an amount up to 1.0% w/v. This is incorporated at the same stage as the AH 11554.

We claim:

1. A compound of the formula:

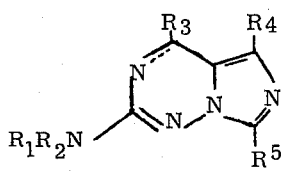

in which
  $R_1$ and $R_2$ may be the same or different, represent a hydrogen atom, or a $C_{1-6}$ alkyl group which may optionally be substituted by a phenyl group, or represent a $C_{1-6}$ alkanoyl group of $C_{1-6}$ alkane sulphonyl group;
  $R_3$ represents a hydrogen atom, or a $C_{1-6}$ alkyl group which may optionally be subtituted by a phenyl group, or represents a $C_{2-6}$ alkenyl group, phenyl, methoxyphenyl, or $C_{1-6}$ alkylthio group;
  $R_4$ represents a hydrogen atom or $C_{1-6}$ alkyl group; and
  $R_5$ represents a hydrogen atom, a $C_{1-6}$ alkyl group, which alkyl group may optionally be substituted by a $C_{3-7}$ cycloalkyl group, or a phenyl group, and physiologically acceptable salts and addition products formed by nucleophilic addition.

2. Compounds as claimed in claim 1 in which $R_1$ represents a hydrogen atom or a methyl, ethyl, propyl, isobutyl, 3-methylbutyl group, or a 3,4-dimethoxybenzyl, phenethyl, formyl, acetyl, butyryl, isovaleryl, benzoyl, 4-chlorobenzoyl or methanesulphonyl group.

3. Compounds as claimed in claim 1 in which $R_2$ represents an ethyl radical.

4. Compounds as claimed in claim 1 in which $R_3$ represents hydrogen, methyl, ethyl, benzyl, phenethyl, phenyl, 4-methoxyphenyl, allyl or methylthio.

5. Compounds as claimed in claim 1 in which $R_4$ represents hydrogen or methyl.

6. Compounds as claimed in claim 1 in which $R_5$ represents propyl, isopropyl, isobutyl, secbutyl, 2-methylbutyl, 3-methylbutyl, cyclopentylmethyl, cyclohexylmethyl or phenyl.

7. Compounds as claimed in claim 1 in the form of physiologically acceptable salts with inorganic or organic acids.

8. Compounds as claimed in claim 1 in the form of addition production formed by nucleophilic addition across the 3,4 bond when this is a double bond, with sodium bisulphite.

9. A compound as claimed in claim 1 which is 2-amino-3,4-dihydro-5-methyl-7-propylimidazo[5.1-f]-as-triazine.

10. A compound as claimed in claim 1 which is 2-amino-3,4-dihydro-5-methyl-7-propylimidazo[5,1-f]-as-triazine, hydrochloride.

11. A compound as claimed in claim 1 which is 2-amino-3,4-dihydro-7-isopropyl-5-methylimidazo[5,1-f]-as-triazine and its hydrochloride.

12. A compound as claimed in claim 1 which is 2-amino-3,4-dihydro-7-isobutyl-5-methylimidazo[5,1-f]-as-triazine and its hydrochloride.

13. A compound as claimed in claim 1 which is 2-amino-3,4-dihydro-5-methyl-7-phenylimidazo[5,1-f]-as-triazine and its hydrochloride.

14. A compound as claimed in claim 1 which is 2-amino-7-cyclohexylmethyl-3,4-dihydro-5-methylimidazo[5,1-f]-as-triazine.

15. A compound as claimed in claim 1 which is 2-amino-7-cyclohexylmethyl-3,4-dihydro-5-methylimidazo[5,1-f]-as-triazine, hydrogen maleate.

16. A compound as claimed in claim 1 which is 2-amino-3,4-dihydro-5-methyl-7(2-methylbutyl)imidazo[5,1-f]-as-triazine and its hydrochloride.

17. A compound as claimed in claim 1 which is 2-amino-7-cyclopenxylmethyl-3,4-dihydro-5-methylimidazo[5,1-f]-as-triazine.

18. A compound as claimed in claim 1 which is 2-amino-3,4-dihydro-7-(3-methylbutyl)imidazo[5,1-f]-as-triazine, hydrochloride.

19. A compound as claimed in claim 1 which is 2-amino-3,4-dihydro-5-methyl-7-(1-methylpropyl)imidazo[5,1-f]-as-triazine and its dihydrochloride.

20. A compound as claimed in claim 1 which is 5-methyl-7-propyl-2-propylaminoimidazo[5,1-f]-as-triazine, hydrochloride.

21. A compound as claimed in claim 1 which is 2-benzylamino-5-methyl-7-propylimidazo[5,1-f]-as-triazine.

22. A compound as claimed in claim 1 which is 5-methyl-2(2-phenethylamino)-7-propylimidazo[5,1-f]-as-triazine and its hydrochloride.

23. A compound as claimed in claim 1 which is 2-isobutylamino-5-methyl-7-propylimidazo[5,1-f]-as-triazine and its hydrochloride.

24. A compound as claimed in claim 1 which is 2-(3,4-dimethoxybenzylamino)5-methyl-7-propylimidazo[5,1-f]-as-triazine.

25. A compound as claimed in claim 1 which is 2-amino-7-isobutyl-5-methylimidazo[5,1-f]-as-triazine.

26. A compound as claimed in claim 1 which is 2-amino-4(p-methoxyphenyl)-5-methyl-7-propylimidazo[5,1-f]-as-triazine and its hydrochloride.

27. A compound as claimed in claim 1 which is 2-amino-4,5-dimethyl-7-propylimidazo[5,1-f]-as-triazine.

28. A compound as claimed in claim 1 which is 2-amino-5-methyl-7-propylimidazo[5,1-f]-as-triazine, hydrochloride.

29. A compound as claimed in claim 1 which is N-(5-methyl-7-propylimidazo[5,1-f]-as-triazine-2-yl) methanesulphonamide.

30. A compound as claimed in claim 1 which is N-(3,4-dihydro-5-methyl-7-propylimidazo[5,1-f]-as-triazin-2-yl)benzamide, hydrogen maleate.

31. A compound as claimed in claim 1 which is N-(3,4-dihydro-5-methyl-7-isobutylimidazo[5,1-f]-as-triazin-2-yl)-p-chlorobenzamide and its hydrochloride.

32. A comound as claimed in claim 1 which is N-(3,4-dihydro-5-methyl-7-propylimidazo[5,1-f]-as-triazin-2-yl)isovaleramide hydrochloride.

33. A compound as claimed in claim 1 which is N-Ethyl-N-(3,4-dihydro-5-methyl-7-propylimidazo[5,1-f]-as-triazin-2-yl)acetamide, hydrochloride.

34. A compound as claimed in claim 1 which is N-(3,4-dihydro-5-methyl-7-propylimidazo[5,1-f]-as-triazin-2-yl)methanesulphonamide, methanesulphonate.

35. A compound as claimed in claim 1 which is N-(3,4-dihydro-5-methyl-7-propylimidazo[5,1-f]-as-triazin-2-yl)acetamide, hydrochloride.

36. A compound as claimed in claim 1 which is N-(3,4-dihydro-7-isobutyl-5-methylimidazo[5,1-f]-as-triazin-2-yl)acetamide.

37. A compound as claimed in claim 1 which is N-(3,4-dihydro-7-isopropyl-5-methylimidazo[5,1-f]-as-triazin-2-yl)acetamide.

38. A compound as claimed in claim 1 which is N-(3,4-dihydro-4,5-dimethyl-7-propylimidazo[5,1-f]-as-triazin-2-yl)acetamide hydrochloride.

39. A compound as claimed in claim 1 which is N-(3,4-dihydro-5-methyl-7-propylimidazo[5,1-f]-as-triazin-2-yl)formamide.

40. A compound as claimed in claim 1 which is N-(3,4-dihydro-5-methyl-7-isobutylimidazo[5,1-f]-as-triazin-2-yl)formamide and its hydrochloride.

41. A compound as claimed in claim 1 which is N-(3,4-dihydro-5-methyl-7-propylimidazo[5,1-f]-as-triazin-2-yl)butyramide, hydrochloride.

42. A compound as claimed in claim 1 which is 3,4-dihydro-5-methyl-7-propyl-2-propylaminoimidazo[5,1-f]-as-triazine, hydrochloride.

43. A compound as claimed in claim 1 which is 2-benzylamino-3,4-dihydro-5-methyl-7-propylimidazo[5,1-f]-as-triazine, hydrochloride.

44. A compound as claimed in claim 1 which is 3,4-dihydro-5-methyl-2(2-phenylethylamino)-7-propylimidazo[5,1-f]-as-triazine, hydrochloride.

45. A compound as claimed in claim 1 which is 3,4-dihydro-2-(3,4-dimethoxybenzylamino)-5-methyl-7-propylimidazo[5,1-f]-as-triazine.

46. A compound as claimed in claim 1 which is 2-Ethylamino 3,4-dihydro-5-methyl-7-propylimidazo[5,1-f]-as-triazine.

47. A compound as claimed in claim 1 which is 3,4-dihydro-2-iso amylamino-5-methyl-7-propylimidazo[5,1-f]-as-triazine and its hydrochloride.

48. A compound as claimed in claim 1 which is 2-methylamino-3,4-dihydro-5-methyl-7-isobutylimidazo[5,1-f]-as-triazine, hydrochloride.

49. A compound as claimed in claim 1 which is 2-amino-3,4-dihydro-5-methyl-4-phenyl-7-propylimidazo[5,1-f]-as-triazine, hydrochloride.

50. A compound as claimed in claim 1 which is 2-amino-3,4-dihydro-4(p-methoxyphenyl)-5-methyl-7-propylimidazo[5,1-as-triazine, hydrochloride.

51. A compound as claimed in claim 1 which is 4-allyl-2-amino-3,4-dihydro-5-methyl-7-propylimidazo[5,1-f]-as-triazine, hydrogen maleate.

52. A compound as claimed in claim 1 which is 2-amino-3,4-dihydro-4,5-dimethyl-7-isobutylimidazo[5,1-f]-as-triazine, hydrochloride.

53. A compound as claimed in claim 1 which is 2-amino-3,4-dihydro-4-ethyl-5-methyl-7-propylimidazo[5,1-f]-as-triazine and its hydrochloride.

54. A compound as claimed in claim 1 which is 2-amino-3,4-dihydro-4,5-dimethyl-7-propylimidazo[5,1-f]-as-triazine and its hydrochloride.

55. A compound as claimed in claim 1 which is N-(4-benzyl-3,4-dihydro-5-methyl-7-propylimidazo[5,1-f]-as-triazin-2-yl)acetamide, hydrochloride.

56. A compound as claimed in claim 1 which is 5-(2-amino-3,4-dihydro-5-methyl-7-propylimidazo[5,1-f]-as-triazin-4-yl)barbituric acid.

57. A compound as claimed in claim 1 which is 5-(2-amino-3,4-dihydro-5-methyl-7-propylimidazo[5,1-f]-as-triazin-4-yl)barbituric acid, hydrochloride.

58. A compound as claimed in claim 1 which is 2-amino-3,4-dihydro-4(4,4-dimethyl-2,6-dioxocyclohexyl)-5-methyl-7-propylimidazo[5,1-f]-as-triazine.

59. A compound as claimed in claim 1 which is 2-amino-3,4-dihydro-4(p-methoxyphenacyl)-5-methyl-7-propylimidazo[5,1-f]-as-triazine, hydrochloride.

60. A compound as claimed in claim 1 which is 2-amino-3,4-dihydro-5-methyl-7-propylimidazo[5,1-f]-as-triazine-4-sulphonic acid.

61. A compound as claimed in claim 1 which is 2-diethylamino-5-methyl-7-propylimidazo[5,1-f]-as-triazine, hydrochloride.

62. A compound as claimed in claim 1 which is 2-amino-5-methyl-4-methylthio-7-propylimidazo[5,1-f]-as-triazine, hydrochloride.

63. The process for the preparation of compounds of the formula:

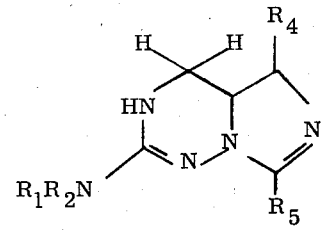

and physiologically acceptable salts and addition products thereof in which $R_1$, $R_2$ which may be the same or different, represent a hydrogen atom, or a $C_{1-6}$ alkyl group which may optionally be substituted by a phenyl group, or represent a $C_{1-6}$ alkanoyl group or $C_{1-6}$ alkane sulphonyl group;

$R_4$ represents a hydrogen atom or a $C_{1-6}$ alkyl group; and $R_5$ represents a hydrogen atom, a $C_{1-6}$ alkyl group, which alkyl group may optionally be substituted by a $C_{3-7}$ cycloalkyl group, or a phenyl group, which comprises the reduction with a metal hydride, diborane or sodium-dihydro-bis(2-methoxymethoxy)aluminate, of a compound having the formula:

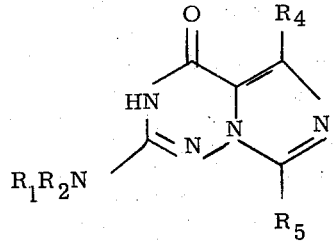

in which $R_1$, $R_2$, $R_4$ and $R_5$ have the meanings given above.

64. A process as claimed in claim 63 in which the reduction is effected with a metal hydride which is lithium aluminium hydride.

* * * * *